United States Patent
Culshaw et al.

(10) Patent No.: US 7,915,264 B2
(45) Date of Patent: Mar. 29, 2011

(54) FUSED PYRIDINE DERIVATIVES FOR USE AS VANILLOID RECEPTOR ANTAGONISTS FOR TREATING PAIN

(75) Inventors: Andrew James Culshaw, London (GB); Peter Gull, Pfeffingen (CH); Allan Hallett, London (GB); Hong-Yong Kim, Whippany, NJ (US); Max Peter Seiler, Riehen (CH); Kaspar Zimmermann, Oberwil (CH); Yugang Liu, Bridgewater, NJ (US); Mahavir Prashad, Montville, NJ (US)

(73) Assignee: Novartis AG, Basel (CH)

( * ) Notice: Subject to any disclaimer, the term of this patent is extended or adjusted under 35 U.S.C. 154(b) by 963 days.

(21) Appl. No.: 10/469,756

(22) PCT Filed: Mar. 25, 2002

(86) PCT No.: PCT/EP02/03332
§ 371 (c)(1), (2), (4) Date: Jan. 6, 2004

(87) PCT Pub. No.: WO02/076946
PCT Pub. Date: Oct. 3, 2002

(65) Prior Publication Data
US 2004/0138454 A1 Jul. 15, 2004

Related U.S. Application Data

(60) Provisional application No. 60/338,281, filed on Dec. 6, 2001.

(30) Foreign Application Priority Data

Mar. 26, 2001 (GB) .................................. 0107505.0

(51) Int. Cl.
*A61K 31/519* (2006.01)
*C07D 471/04* (2006.01)

(52) U.S. Cl. ....................................... 514/258; 544/279
(58) Field of Classification Search .................. 544/285, 544/279; 514/249, 258
See application file for complete search history.

(56) References Cited

U.S. PATENT DOCUMENTS 2,749,344 A 6/1956 Hitchings et al. .......... 260/256.4
5,958,930 A 9/1999 Gangjee

FOREIGN PATENT DOCUMENTS

WO WO 95/18616 A2 7/1995
WO WO 98/02162 1/1998

OTHER PUBLICATIONS

Hcaplus77:88424.*
Hcaplus 138:70679.*
Chemical Abstract No. 133:261086 & M. Oguchi et al., J.Med. Chem., No. 43 (16), pp. 3052-3066 (2000).
Chemical Abstract No. 132:78525 & J.Y.Liu et al., Youji, Hauxue, No. 19(6), pp. 582-586 (1999).
Wall, Mark et al., Journal of Medicinal Chemistry, "A Multisubstrate Adduct Inhibitor of AICAR Transformylase", vol. 42, No. 18, , pp. 3421-3424 (1999).
McIntyre P. et al., British Journal of Pharmacology, "Pharmacological differences between the human and rat vanilloid receptor 1 (VRI)", No. 321, pp. 1084-1094 (2001).
Bae et al, *Tetrahedron Lett*, vol. 41, No. 31, pp. 5899-5902 (2000).
Dave et al., *Indian J Pharma Sci*, vol. 48, No. 3, pp. 75-77 (1986).
Fox et al., *JACS*, vol. 122, pp. 1360-1370 (2000), and supporting information.
Korte et al., *Chem Ber*, vol. 85, pp. 1012-1019 (1952).
Martin et al., *Tetrahedron*, vol. 50, No. 7, pp. 2255-2264 (1994).
Matyus et al., *Leibigs Ann Chem*, vol. 10, pp. 1653-1661 (1984).
PCT search report for PCT/EP 02/03332, Sep. 23, 2002.
Petrow et al., *J Chem Soc*, pp. 1389-1392 (1948).
Robins et al., *J Am Chem Soc*, vol. 77, pp. 2256-2259 (1955).
Robins et al., *J Am Chem Soc, Am Chem Soc*, vol. 80, No. 13, pp. 3449-3457 (1958).
Roh et al., *Synth Comm*, vol. 30, No. 1, pp. 81-86 (2000).
Trattner et al., *J Org Chem, Am Chem Soc*, vol. 29, pp. 2674-2677 (1964).
Troschuetz et al., *Arch Pharm*, vol. 311, No. 5, pp. 406-414 (1978).
Tschitschibabin et al., *Chem Ber*, vol. 60, p. 775 (1927).

* cited by examiner

*Primary Examiner* — Charanjit S Aulakh

(57) ABSTRACT

The invention provides compounds of formula (I) wherein $R^1, R^2, R^3, R^4$, and $R^5$ are as defined in the description, and the preparation thereof. The compounds of formula (I) are useful as pharmaceuticals.

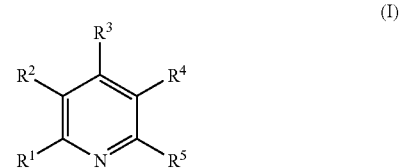

(I)

6 Claims, No Drawings

FUSED PYRIDINE DERIVATIVES FOR USE AS VANILLOID RECEPTOR ANTAGONISTS FOR TREATING PAIN

The present invention relates to novel pyridine derivatives, to processes for their production, their use as pharmaceuticals and to pharmaceutical compositions comprising them.

More particularly the present invention provides a compound of formula I

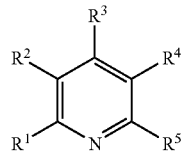

(I)

wherein
$R^1$ and $R^2$ together are —NH—C(SR$^6$)=N—C(O)—, —NR$^7$—C(R$^8$)=N—C(O)—, —N=C(SR$^9$)—NR$^{10}$—C(O)—, —NR$^{11}$—X—NR$^{12}$C(O)—, —NH—X—NH—, —NH—X—N=C(R$^{13}$)—, —NH—X—NH—CH$_2$—, —N=Z—NH—, —N=Z—NH—CH$_2$—, —N=Z—NH—C(O)— and —N=Z—N=C(R$^{14}$)—, wherein X is C(O), C(S) or C(O)—C(O); Z is N or CR$^{15}$, R$^6$ is $C_1$-$C_4$alkyl; R$^7$ and R$^8$ are each independently hydrogen, $C_1$-$C_4$alkyl, $C_3$-$C_8$cycloalkyl or form together with the adjacent atoms a 5 or 6 membered heterocyclic ring; R$^9$ and R$^{10}$ together are $C_1$-$C_4$alkylene; R$^{11}$ is hydrogen; $C_1$-$C_4$alkyl; $C_1$-$C_4$alkyl substituted by C(O)OC$_1$-$C_4$alkyl; or phenyl substituted by $C_1$-$C_4$alkyl; R$^{12}$ is hydrogen, NH$_2$; $C_1$-$C_4$alkyl; or phenyl substituted by $C_1$-$C_4$alkyl; R$^{13}$ is hydrogen, halogen, NH$_2$ or $C_1$-$C_4$alkoxy; R$^{14}$ is hydrogen, hydroxy, halogen, NH$_2$, $C_1$-$C_4$alkyl or $C_1$-$C_4$alkoxy; and R$^{15}$ is hydrogen, halogen, $C_1$-$C_4$alkyl, $C_1$-$C_4$alkoxy or SCH$_2$C(O)OC(CH$_3$)$_3$;
$R^3$ is hydrogen; OH; CN; $C_1$-$C_6$alkyl; phenyl; or C(O)OC$_1$-$C_4$alkyl;
$R^4$ is hydrogen; halogen; NH$_2$; CN; $C_1$-$C_6$alkyl; $C_1$-$C_6$alkyl substituted by OH; phenyl; phenyl substituted by OH, halogen, $C_1$-$C_6$alkyl, $C_1$-$C_6$haloalkyl or $C_1$-$C_6$alkoxy; benzyl; benzoyl substituted by OH; or C(O)OC$_1$-$C_6$alkyl; 5 or 6 membered aromatic or aliphatic heterocyclic ring;
$R^5$ is hydrogen; OH; NH$_2$; halogen; $C_1$-$C_6$alkyl; $C_1$-$C_6$alkyl substituted by halobenzyl; $C_3$-$C_6$cycloalkyl; phenyl; pyridinyl; NHC$_1$-$C_4$alkyl; or N=CHN(C$_1$-$C_4$alkyl)$_2$;
with the proviso that compounds of formula I are not pyrido[3,2-d]pyrimidine-2,4(1H,3H)-dione and 6-chloro-2-methyl-4-oxo-pyrido[3,2-d]pyrimidine;
in free base or acid addition salt form.

Compounds of the invention exist in free or salt, e.g. acid or base addition salt form. The invention is to be understood as including the compounds of formula I in free as well as in salt form, e.g. as trifluoroacetate or hydrochloride salt. Suitable pharmaceutically acceptable acid addition salts for pharmaceutical use in accordance with the invention include in particular the hydrochloride salt.

More particular examples for $R^1$ and $R^2$ include —NR$^{11}$C(O)NR$^{12}$C(O)—, —NHC(S)NHC(O)—, —NH—C(O)—NH—, —NH—C(S)—NH—, —NH—C(O)—C(O)—NH—, —NH—C(O)—N=C(Cl)—, —NH—C(O)—N=C(OCH$_3$)—, —NH—C(O)—N=C(NH$_2$)—, —NH—C(O)—N=CH—, —NH—C(O)—NH—CH$_2$—, —NH—C(SCH$_3$)=N—C(O)—, —N=CH—NH—, —N=N—NH—, —N=CH—NH—CH$_2$—, —N=C[SCH$_2$C(O)OC(CH$_3$)$_3$]—NH—C(O)—, —N=CH—NH—C(O)—, —N=C(Cl)—NH—C(O)—, —N=C(NH$_2$)—NH—C(O)—, —N=C(CH$_3$)—NH—C(O)—, —N=C(Cl)—N=C(Cl)—, —N=C(Cl)—N=C(NH$_2$)—, —N=C(OCH$_3$)—N=C(OCH$_3$)—, —N=C(OCH$_3$)—N=C(NH$_2$)—, —N=CH—N=C(NH$_2$)—, —N=CH—N=CH—,

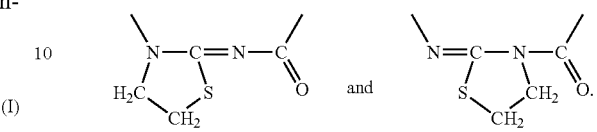

A 5 or 6 membered aromatic or aliphatic heterocyclic ring for $R^4$ may be e.g. but not limited to thiophenyl, furyl, imidazolyl, pyridinyl, pyrimidinyl, pyrrolidinyl, piperidinyl, piperizinyl and derivatives thereof (e.g. $C_1$-$C_4$alkyl, OC$_1$-OC$_4$alkyl, halogenyl, etc.).

Alkyl groups in the compounds of formula I may be branched or straight chain.

In formula I the following significances are preferred independently, collectively or in any combination or sub-combination:
(a) $R^1$ and $R^2$ together are a divalent group —NHC(O)NHC(O)— or —NHC(S)NHC(O)—;
(b) $R^3$ is hydrogen;
(c) $R^4$ is phenyl; phenyl substituted by OH, halogen, e.g. chloride, fluoride, $C_1$-$C_6$alkyl, $C_1$-$C_6$haloalkyl or $C_1$-$C_6$alkoxy; and
(d) $R^5$ is branched or un-branched $C_1$-$C_6$alkyl, e.g. isopropyl, tert. butyl or $C_3$-$C_6$cycloalkyl.

Most preferred are compounds of formula I wherein $R^1$ and $R^2$ together are —NH—C(S)—NH—C(O)—; $R^3$ is hydrogen; $R^4$ is phenyl; or phenyl substituted by halogen, $C_1$-$C_4$alkyl, $C_1$-$C_4$haloalkyl or $C_1$-$C_4$alkoxy; and $R^5$ is $C_1$-$C_4$alkyl; or $C_6$cycloalkyl.

The invention also provides a process for the production of a compound of formula I comprising the step of reacting a compound of formula II

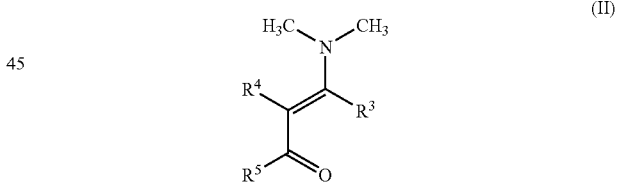

(II)

wherein $R^3$, $R^4$ and $R^5$ have the above meanings;
with a compound of formula III

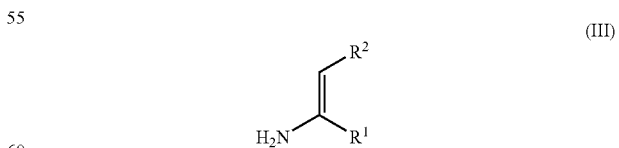

(III)

wherein $R^1$ and $R^2$ have the above meanings;
and recovering the obtained compound, in free base or in acid addition salt form.

Compounds of formula I resulting from the above process may be further derivatised, e.g. by reacting a compound of formula I' wherein $R^3$, $R^4$ and $R^5$ have the above meanings and $R^1$ and $R^2$ together are a group —N=C(OH)—N=C(OH)— with, e.g. phosphorous oxychloride to give a compound of formula I wherein $R^3$, $R^4$ and $R^5$ have the above meanings and $R^1$ and $R^2$ together are a group —N=C($R^{15'}$)—N=C($R^{14'}$)— wherein $R^{1'}$ is Cl and $R^{15'}$ is OH or wherein $R^{14'}$ and $R^{15'}$ are Cl. These two compounds may be further derivatised by standard procedures to give compounds of formula I wherein $R^3$, $R^4$ and $R^5$ have the above meanings and $R^1$ and $R^2$ together are a group —N=C($R^{15}$)—N=C($R^{14}$)— wherein $R^{14}$ and $R^{15}$ have the above meanings.

Compounds of formula I wherein $R^3$, $R^4$ and $R^5$ have the above meanings and $R^1$ and $R^2$ together are a group —N=C(Cl)—N=C(Cl)— may be reacted with hydrogen under standard conditions to give compounds of formula I wherein $R^3$, $R^4$ and $R^5$ have the above meanings and $R^1$ and $R^2$ together are a group —N=CH—NH—$CH_2$—.

In general, the reactions may be carried out in accordance with standard procedures. However, the yield to obtain compounds of formula I is improved by minimizing the hydrolysis of the enamine back to ketone, e.g. to 1-(4-chlorophenyl)-3,3-dimethyl-2-butanone. During the reaction for the first 12-20 hours, the temperature of the reaction solution is kept below 75° C., preferably below 73° C. Then the reaction is heated to about 100° C. for 2-4 hours, preferably 3 hours. The solvent is removed using a toluene-heptane mixture. Other solvent mixtures can be of an aromatic hydrocarbon solvent with a lower aliphatic hydrocarbon ($C_3$-$C_8$) solvent. Aqueous workup followed by precipitation gives the free base. The salt forms are made by standard procedures known to the skilled artisan, e.g. 6-(4-chlorophenyl)-7-(1,1-dimethylethyl)-2,3-dihydro-2-thioxo-pyrido[2,3-d]pyrimidine-4(1H)-one is purified either as the potassium salt, followed by conversion to the free acid form and recrystallization from ethanol and water or by isolating the crude free acid form followed by the recrystallization from ethanol and water. Compounds of formula I may be further derivatised to arrive at different compounds of formula I.

Compounds of formula II may be prepared e.g. in a first step by Pd-catalyzed arylation of pinacolone with 4-bromochlorobenzene in toluene in the presence of sodium t-butoxide (1.5-3.0 equivalents) to a ketone intermediate. The Pd catalyst is Palladium acetate or other palladium catalysts, such as e.g. $Pd_2(dba)_3$. The sodium t-butoxide serves as a base, and other suitable bases such as lithium bis(trimethylsilyl)amide, sodium bis(trimethylsilyl)amide can be used. This reaction is conducted in a toluene solution. Other solvents can be THF, xylene. The reaction temperature is at about 80-110° C. The crude product in toluene solution is used directly in the next step after extractive removal of palladium by treatment with an aqueous solution of L-cysteine and sodium thiosulfate and azeotropic removal of water. Other methods which serve to remove the catalyst such as charcoal can also be employed. In a second step, the ketone intermediate is e.g. reacted with N,N-dimethylformamide dimethyl acetal to prepare the enamine intermediate, 2-(4-chlorophenyl)-1-(dimethylamino)-4,4-dimethyl-1-penten-3-one. This step takes place preferably in toluene, or another suitable aromatic or aliphatic hydrocarbon solvent, at reflux temperature. Compounds of formula II may be e.g. prepared as illustrated in example 1 and 2.

Starting compounds of formula III are known or may be prepared from corresponding known compounds or may be e.g. prepared as illustrated in example 1 and 2.

The compounds of the invention and their pharmaceutically acceptable acid addition salts (hereinafter the agents of invention) have pharmacological activity and are useful as pharmaceuticals. In particular the agents of invention are functional blockers of the human vanilloid receptor 1 (hVR1).

Vanilloid receptor interaction of the agents of invention may be demonstrated by their ability to block ion flow through vanilloid receptor 1 ion channels, e.g. by measuring intracellular calcium levels by e.g. a fluorometric determination of calcium with a calcium sensitive dye, such as by the FLIPR method, or by determining $^{45}$Ca-uptake or $^{14}$C-guanidinium efflux, as demonstrated in accordance with the following test method.

Fluorescence assay: Cultures of Chinese Hamster Ovary (CHO) cells expressing human vanilloid receptor 1 ion channels are prepared according to standard protocols [McIntyre et al., British Journal of Pharmacology 132: 1084-1094 (2001)]. The activity of test compounds are investigated using a fluorescence assay utilising calcium sensitive dyes to measure changes in $[Ca^{2+}]i$. The cells are plated at a density of 25,000 per well on 96 well Costar black, clear bottomed plates cultured at 37° C. in 5% $CO_2$ in MEM medium overnight. On the day of the assay, cells are incubated in either 2 µM fura-2/AM or 2 µM fura-6F (Molecular Probes) made up in assay buffer [Hank's Balanced Salt Solution (HBSS, Invitrogen) containing 10 mM N-2-(hydroxyethylpiperazine-N'-[2-ethanesulfonic acid) (HEPES), pH 7.4] containing 0.01% pluronic F-127 for 30 min at room temperature. After washing twice with assay buffer 100 µl assay buffer, or test compounds (range from 1 nM to 10 µM final) where appropriate, are added to each well and the plate placed in a Molecular Devices Flexstation. The fluorescence is measured over 1 min at 4 s intervals using excitation wavelengths of 340 and 380 nm and emission of 520 nm. Human vanilloid receptor 1 ion channels are stimulated by application of either the agonist capsaicin or low pH. At approximately 17 s, 20 µl of capsaicin made up at 6 fold the required final concentration were transferred to the cells. For pH experiments, 100 µl HBSS alone pH 7.4 (containing test compounds) is added to the cells and 20 µl of 60 mM 2-[N-morpholino]ethane sulfonic acid (MES) in HBSS transferred to the cells. The pH of this solution is adjusted such that it gives the desired pH when diluted 1:6. The ratio of fluorescence intensities following excitation at 340 and 380 nm is calculated for each time point. The agonist-evoked response is calculated as the mean of the ratios in the four time-points following stimulation minus the basal ratio.

The agents of invention in the above test effectively block Ca-uptake in the range from 1 nM to 10 µM.

Activity specifically as analgesic agents may be demonstrated in accordance with standard test methods, e.g. as described in the following test.

Test: Anti-Hyperalgesic Effects in a Model of Neuropathic Pain in the Rat

The agents of invention are potent and efficacious anti-hyperalgesic agents following oral administration in the following rat model of neuropathic pain. Peripheral neuropathy is induced by partial ligation of the left sciatic nerve. Mechanical hyperalgesia is assessed from paw withdrawal thresholds measured on the ipsilateral (ligated) and contralateral (non-ligated) hindpaws using standard paw pressure methods. Drug effects are studied 11-15 days post ligation. The mean paw withdrawal threshold±s.e.m. for the left (ligated) paw is compared to that of the right (non-ligated) paw.

The agents of invention are administered, e.g. orally in 20% cremophor/water in a volume of 1 ml. The post-drug percentage hyperalgesia values are obtained by comparison to the pre-drug value for the right (non-ligated) paw; this enables a true measure of the reduction in hyperalgesia to be obtained without the added complication of any drug effects on the right paw. Single oral administration of the agents of invention produces a highly effective reversal of mechanical hyperalgesia in the partially denervated rat hind paw. The agents of invention produce a reversal of mechanical hyperalgesia at 0.1-100 mg/kg and show a rapid onset of activity with a long duration of action.

The agents of invention are accordingly useful as vanilloid receptor blockers, e.g. in the treatment of diseases and conditions in which vanilloid receptor activation plays a role or is implicated. Such conditions include in particular pain, e.g. bone and joint pain (osteoarthritis), cancer pain, myofascial pain (muscular injury, fibromyalgia) and perioperative pain (general surgery, gynecologic surgery).

The agents of invention are particularly useful in the treatment or prevention of chronic pain, especially inflammatory, e.g. chronic inflammatory pain, inflammatory diseases for example inflammatory airways disease, e.g. (Chronic Obstructive Pulmonary Disease) COPD, or in asthma, cough, urinary incontinence, migraine, visceral disorders (e.g. inflammatory bowel disease), rhinitis, cystitis, e.g. interstitial cystitis, pancreatitis, uveitis, inflammatory skin disorders and rheumatoid arthritis.

The agents of invention are thus useful as vanilloid receptor antagonists, e.g. for the treatment of pain of various genesis or aetiology and as anti-inflammatory and/or anti-oedemic agents for the treatment of inflammatory reactions, diseases or conditions, as well as for the treatment of allergic responses. Having regard to their analgesic/ant-inflammatory profile they are useful for the treatment of inflammatory pain, for the treatment of hyperalgesia and, in particular, for the treatment of severe chronic pain. They are, for example, useful for the treatment of pain, inflammation and/or oedema consequential to trauma, e.g. associated with burns, sprains, fracture or the like, subsequent to surgical intervention, e.g. as post-operative analgesics, as well as for the treatment of inflammatory pain of diverse genesis, e.g. for the treatment of osteo and rheumatoid arthritis and rheumatic disease, tenosynovitis and gout. They are further suitable as analgesics for the treatment of pain associated with, e.g., angina, menstruation or cancer. As anti-inflammatory/ant-oedema agents, they are further useful, e.g., for the treatment of inflammatory skin disorders, for example psoriasis and eczema.

As vanilloid receptor blockers, the agents of invention are also useful as smooth muscle relaxants, e.g. for the treatment of spasm of the gastro-intestinal tract or uterus, e.g. in the therapy of Crohn's disease, ulcerative colitis or pancreatitis.

The agents of invention are in particular useful as agents for the therapy of airways hyperreactivity and for the treatment of inflammatory events associated with airways disease, in particular asthma. In addition, the agents of invention may, for example, be used for the control, restriction or reversal of airways hyperreactivity in asthma.

Inflammatory or obstructive airways diseases to which the present invention is applicable include asthma of whatever type or genesis including both intrinsic and, especially, extrinsic asthma. Thus, the agents of invention are useful for the treatment of allergic asthma, as well as, for example, exercise induced asthma, occupational asthma, asthma induced following bacterial infection, other non-allergic asthmas and "wheezy-infant syndrome".

Efficacy in the treatment of asthma will be evidenced by reduced frequency or severity of symptomatic attack, e.g. of acute asthmatic or bronchoconstrictor attack and by reduced requirement for other, symptomatic therapy, for example anti-inflammatory (e.g. corticosteroid) or bronchodilator (e.g. $\beta_2$ adrenergic) therapy.

Inflammatory or obstructive airways diseases to which the present invention is applicable further include pneumoconiosis (an inflammatory, commonly occupational, disease of the lungs, frequently accompanied by repeated inhalation of dusts) of whatever type or genesis, including, for example, aluminosis, anthracosis, asbestosis, chalicosis, ptilosis, siderosis, silicosis, tabacosis and, in particular, byssinosis.

Further inflammatory or obstructive airways diseases and conditions for which the agents of invention may be used include adult respiratory distress syndrome (ARDS), chronic obstructive pulmonary or airways disease (COPD or COAD), and bronchitis. The agents of invention may also be used for the treatment of allergic and vasomotor rhinitis.

In addition to the foregoing the agents of invention are also indicated for use in the therapy of septic shock, e.g. as anti-hypovolaemic and/or anti-hypotensive agents, in the treatment of inflammatory bowel disease cerebral oedema, headache, migraine and inflammatory skin disease such as eczema and psoriasis, and inflammatory disorders of the gut, e.g. irritable bowel syndrome, Crohn's disease, ulcerative colitis, cystitis, e.g. interstitial cystitis, nephritis, uveitis.

The agents of the invention can be administered in vivo either alone or in combination with other pharmaceutical agents effective in the treatment of diseases and conditions in which vanilloid receptor activation plays a role or is implicated including cyclooxygenase-2 (COX-2) inhibitors, such as specific COX-2 inhibitors (e.g. celecoxib and rofecoxib) and nonsteroidal anti-inflammatory drugs (NSAIDs) (e.g. acetylsalicylic acid, Propionic acid derivatives), tricyclic antidepressants (e.g. Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®), anticonvulsants (e.g. carbamazepine, oxcarbazepine, gabapentin), bradykinin B1 or B2 antagonists and $GABA_B$ agonists (e.g. L-baclofen).

The pharmaceutical compositions for separate administration of the combination partners and for the administration in a fixed combination, i.e. a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carries, especially suitable for enteral or parenteral application.

For the above indications the appropriate dosage of the agents of invention will, of course, vary depending upon, for example, the host, the mode of administration and the nature and severity of the condition being treated as well as the relative potency of the particular agent of invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg, conveniently administered once or in divided doses up to 4× per day or in sustained release form. Oral dosage forms accordingly suitably comprise from about 0.2 or 2.0 to about 700 or 1400 mg agent of invention admixed with an appropriate pharmaceutically acceptable diluent or carrier therefore.

The agents of invention may alternatively be administered e.g. topically in the form of a cream, gel or the like for example for the treatment of conditions of the skin as hereinbefore described or by inhalation, e.g. in dry powder form, for example for the treatment of asthma.

Examples for compositions comprising the agents of invention include, e.g. a solid dispersion, an aqueous solution, e.g. containing a solubilising agent, e.g. cyclodextrin, a microemulsion and a suspension of, e.g. a micronized hydrochloride salt of a compound of formula I in, e.g. aqueous methyl cellulose in the range of from 0.1 to 1%, e.g. 0.5%. The composition may be buffered to, e.g. a pH in the range of from 3.5 to 9.5, e.g. to pH 4.5, by a suitable buffer, e.g. malic acid.

The agents of invention are also useful as research chemicals.

In accordance with the foregoing the present invention also provides:

(1) A compound of formula I in free base or pharmaceutically acceptable acid addition salt form for use as a vanilloid receptor blocker, for example for use in any of the particular indications hereinbefore set forth;
(2) A pharmaceutical composition comprising a compound of formula I in free base or pharmaceutically acceptable acid addition salt form as under (1) as active ingredient together with a pharmaceutically acceptable diluent or carrier therefore;
(2') A compound of formula I in free base or pharmaceutically acceptable acid addition salt form for the treatment or prevention of a disease or condition in which vanilloid receptor plays a role or is implicated comprising a compound of formula I and a carrier.
(3) A method for the treatment of any of particular indication hereinbefore set forth in a subject in need thereof which comprises administering an effective amount of a compound of formula I in free base or pharmaceutically acceptable acid addition salt form as under (1);
(3') A method for treating or preventing a disease or condition in which vanilloid receptor plays a role or is implicated comprising administering to a mammal in need thereof a therapeutically effective amount of a compound of formula I in free base or pharmaceutically acceptable acid addition salt form.
(4) Use of a compound of formula I in free base or pharmaceutically acceptable acid addition salt form for the manufacture of a medicament for the treatment or prevention of a disease or condition in which activity of vanilloid receptor plays a role or is implicated;
(5) A process for the preparation of a compound of formula I in free base or pharmaceutically acceptable acid addition salt form as under (1);
(6) A method as defined above comprising co-administration, e.g. concomitantly or in sequence, of a therapeutically effective amount of a vanilloid receptor antagonist, e.g. a compound of formula I in free base or pharmaceutically acceptable acid addition salt form and a second drug substance, said second drug substance being for example for use in any of the particular indications hereinbefore set forth;
(7) A combination comprising a therapeutically effective amount of a compound of formula I in free base or pharmaceutically acceptable acid addition salt form and a second drug substance, said second drug substance being for example for use in any of the particular indications hereinbefore set forth.

The preferred compound of formula I is the 7-.tert.-butyl-6-(4-chlorophenyl)-2-thioxo-2,3-dihydro-1.H.-pyrido[2,3-.d.]-pyrimidin-4-one (example 2). This compound is a potent vanilloid receptor 1 (VR1) ion channel blocker in vitro (IC$_{50}$ for human VR1 in the fluorescence assay=65.1 nM; for rat VR1=19.2 nM). In the above-mentioned neuropathic pain model in the rat, it dose-dependently reduces paw withdrawal thresholds for at least 6 h when administering as a single dose at 0.3-30 mg/kg p.o. after the establishment of hyperalgesia.

The following examples illustrate the invention.

In the examples the following abbreviations are used: DMF: dimethyl formamide; RT: room temperature; THF: tetrahydrofuran; LCMS: Liquid Chromatagrophy mass spectrometry

EXAMPLE 1

Preparation of 6-benzyl-7-isopropyl-1.H.-pyrido[2,3-.d.]pyrimidine-2,4-dione (a) Lithium chloride (27 mmol) and copper (I) chloride (13.46 mmol) are weighed into a flame dried 250 mL round-bottomed flask fitted with low temperature thermometer. Dry THF (50 mL) is added and the mixture stirred at RT for 1 h to give a cloudy yellow-green solution. This is cooled to −55° C. and isopropylmagnesium chloride (6.75 mL of a 2 M solution in THF, 13.5 mmol) is added. After 15 min hydrocinnamoyl chloride (13.46 mmol) is added quickly at −60° C. and the mixture allowed to warm slowly to RT overnight. The mixture is quenched with water (100 mL) and 35% ammonium hydroxide (20 mL) is added. The mixture is stirred at RT for 1 h and then extracted with diethyl ether (3×50 mL). The combined ether extracts are washed with saturated brine (50 mL), dried (MgSO$_4$), filtered and evaporated under reduced pressure to give 4-methyl-1-phenyl-pentan-3-one.

(b) 4-Methyl-1-phenyl-pentan-3-one (10.2 mmol) and tert.-butoxybis-(dimethylamino)-methane (16 mmol) are mixed and heated together at 110° C. for 17 h. Excess reagent is removed under reduced pressure to give (E/Z)-2-benzyl-1-dimethylamino-4-methyl-pent-1-en-3-one.

(b) (E/Z)-2-Benzyl-1-dimethylamino-4-methyl-pent-1-en-3-one (8.66 mmol) and 4-amino-2,6-dihydroxypyrimidine (10.7 mmol) are mixed in ethanol (10 mL) and 10% aqueous acetic acid (90 mL). The mixture is heated at 120° C. under an atmosphere of dry nitrogen for 18 h, cooled to RT and the colourless solid formed is recovered by filtration. Recrystallisation from 10% glacial acetic acid in isopropanol gives 6-benzyl-7-isopropyl-1.H.-pyrido[2,3-.d.]pyrimidine-2,4-dione. LCMS: MH+ 296; >97% pure at 214 and 254 nm, Retention time=5.72 min.

EXAMPLE 2

Preparation of 7-.tert.-butyl-6-(4-chlorophenyl)-2-thioxo-2,3-dihydro-1.H.-pyrido[2,3-.d.]pyrimidin-4-one (a) 4-Chlorobenzyl bromide (0.1 mol) and dry diethyl ether (200 mL) are placed in a flame-dried, 2-necked round bottomed flask at RT. The solution is stirred under an inert atmosphere while magnesium turnings (0.1 mol) are added portionwise. Trimethylacetonitrile (0.1 mol) is then added, followed by dry m-xylene (100 mL). The reaction is stirred at RT for 1 h and then the diethyl ether is distilled off (oil bath temp. 130° C.). A further portion of trimethylacetonitrile (5 mL) is added and the resulting suspension is heated at reflux overnight under an atmosphere of dry nitrogen. The reaction mixture is cooled to 0° C. and a solution of concentrated hydrochloric acid (22 mL) in water (40 mL) is added slowly.

The resulting solid is filtered off and dried under vacuum to give 1-(4-chlorobenzyl)-2,2-dimethyl-propylideneamine hydrochloride.

(b) 1-(4-Chlorobenzyl)-2,2-dimethyl-propylideneamine hydrochloride (61 mmol) is suspended in 2 N aqueous hydrochloric acid (200 mL) and heated at reflux for 3 h. The resulting biphasic mixture is cooled to RT, extracted with dichloromethane (3×) and the combined DCM extracts dried (MgSO$_4$) and evaporated under reduced pressure to give 1-(4-chlorophenyl)-3,3-dimethyl-butan-2-one.

(c) 1-(4-Chlorophenyl)-3,3-dimethyl-butan-2-one (30 mmol) and tert-butoxybis-(dimethylamino)methane (31.5 mmol) are heated together at reflux overnight. The reaction mixture is then cooled to RT and the excess tert-butoxybis(dimethylamino)methane removed under reduced pressure to give 2-(4-chlorophenyl)-1-dimethylamino-4,4-dimethyl-pent-1-en-3-one.

(d) 2-(4-Chlorophenyl)-1-dimethylamino-4,4-dimethyl-pent-1-en-3-one (30 mmol) is dissolved in ethanol (20 mL) and added dropwise to a stirred slurry of 4-amino-6-hydroxy-2-mercaptopyrimidine monohydrate (31.5 mmol) in 10% aqueous acetic acid (200 mL). The mixture is then heated at reflux temperature overnight. The condenser is then removed and the ethanol allowed to boil off over 2 h. The reaction mixture is cooled to RT and the solid that has formed is recovered by filtration and washed with ice-cold water. The solid is then dissolved in methanol, filtered to remove unwanted by-product and the methanol solution concentrated under reduced pressure to induce crystallisation. The crystals formed are collected and dissolved in diethyl ether, filtered to remove insoluble by-product and evaporated to dryness. The resulting solid is dried under vacuum for 3 days to give 7-.tert.-butyl-6-(4-chlorophenyl)-2-thioxo-2,3-dihydro-1.H.-pyrido[2,3-.d.]-pyrimidin-4-one. Retention 7.25 min [Phenomenex C18 R HPLC analytical column, 30 mm×4.6 mm, gradient 90:10 to 0:100 (water+0.1% TFA:MeCN) over 10 min]; NMR d6-DMSO (400 MHz, referenced to residual DMSO at δ2.5) δ 1.17 (s, 9H), 7.37 (d, 2H), 7.5 (d, 2H), 7.75 (s, 1H), 12.56 (s, 1H), 13.07 (s, 1H) [M+H]+ 346/348.

or alternatively:

(a') A 5 L, 4-necked, round-bottomed flask, equipped with a mechanical stirrer, digital thermometer, addition funnel, heating mantle and a condenser with nitrogen inlet-outlet, is charged with 100.0 g of sodium t-butoxide and 300 mL of dry toluene. The mixture is stirred at 23-27° C. and added to a solution of 1.48 g of palladium acetate and 125.0 g of 4-bromochlorobenzene in 850 mL of dry toluene. The mixture is heated to a temperature at 95-100° C. using a heating mantle temperature set at about 95-125° C. over a period of 40 minutes. A solution of 98.1 g of pinacolone in 300 mL of toluene is added over a period of 45 minutes to 1 hour while maintaining the internal temperature at 95-100° C. The mixture is stirred for an additional 9 hours, then cooled to an internal temperature at 23-25° C. over a period of 30 minutes. Six hundred (600) g of 15% ammonium chloride solution is added over a period of 10 minutes while maintaining the internal temperature at 20-27° C. The mixture is stirred, the organic layer separated, and washed with 600 mL of saturated sodium chloride solution. The organic layer is charged into a 5 L, 4-necked, round-bottomed flask equipped with a mechanical stirrer, digital thermometer, addition funnel, heating mantle and a condenser with nitrogen inlet-outlet, and a solution of 150.0 g of L-cysteine in 900 mL of water is added. The mixture is heated to an internal temperature at 84-90° C. over a period of 40 minutes to achieve reflux, then stirred for an additional 5 hours. After cooling, the aqueous layer is removed, and the organic layer filtered over a Buchner funnel containing a pad of 20.0 g of Celite. After washing the Celite pad with 200 mL of toluene, and saving the filtrate, to the filtrate is added a solution of 75.0 g of L-cysteine and 2.5 g of sodium thiosulfate pentahydrate in 600 mL of water. The mixture is heated to an internal temperature at 78-82° C. White solids formed gradually. The triphasic mixture is stirred at this temperature for an additional 5 hours, then cooled, and the organic layer is separated. The organic layer is filtered over a pad of 20.0 g of Celite and the pad is washed with 200 mL of toluene. The combined filtrates is washed again with 400 mL of saturated NaCl solution. The organic layer is filtered and concentrated to collect about 800 mL of solvent to afford about 1.0 L of crude 1-(4-chlorophenyl)-3,3-dimethyl-2-butanone in toluene, which is used directly in the next step, theoretical Yield: 137.6 g (Pd 2 ppm).

(b') A 3 L, 4-necked, round-bottomed flask, equipped with a mechanical stirrer, digital thermometer, reflux condenser, and nitrogen inlet-outlet, is charged with 953 g (1.05 L) of a toluene solution containing 1-(4-chlorophenyl)-3,3-dimethyl-2-butanone and 173 g (200 mL) of toluene; then add by pump 232 g (259 mL) of N,N-dimethylformamide dimethyl acetal. The solution is heated to an internal temperature at 97-109° C. (reflux) and stirred at this temperature for 5 hours. One hundred (100) mL of solvent is distilled off over a period of 0.5 hours. After distillation is stopped, the mixture is heated to an internal temperature at 107-114° C. (reflux). The mixture is stirred at this temperature for an additional 1 hour. Three more distillations follow in a similar procedure. Then the reaction mixture is cooled to an internal temperature at 20-25° C. over 1 hour, and stirred at this temperature for 1 hour, filtered over a pad of 70 g of Celite and the pad was washed with 300 mL of toluene. Filtrates are combined and concentrated under vacuum (30-80 torr) at an internal temperature at 25-40° C. (maximum jacket temperature 50° C.) to collect about 800 g or 925 mL of solvent to afford 275 g of crude 2-(4-chlorophenyl)-1-(dimethylamino)-4,4-dimethyl-1-pentene-3-one (Theoretical yield: 173.6 g). This crude product is dissolved in 440 mL (380 g) of toluene and the removal of excess N,N-dimethylformamide dimethyl acetal is confirmed by $^1$H NMR. The solution can be held at 21-23° C. under nitrogen and then used in the next step.

(c') A 3 L, 4-necked, round-bottomed flask equipped with a mechanical stirrer, digital thermometer, reflux condenser, nitrogen inlet-outlet, and addition funnel is charged with 84.3 g of 4-amino-6-hydroxy-2-mercaptopyrimidine monohydrate and 655 mL (687 g) of acetic acid. The suspension is stirred at an internal temperature at 22-25° C. for 30 minutes. Six hundred fifty-five (655) g of a toluene solution of 2-(4-chlorophenyl)-1-(dimethylamino)-4,4-dimethyl-1-pentene-3-one is added over a period of 30 minutes while maintaining the internal temperature at 22-30° C. (slightly exothermic). The addition funnel is washed with 100 mL of toluene in two equal portions of 50 mL each and added to the reaction mixture. The mixture is heated to an internal temperature at 70±3° C., and stirred at this temperature for 15 hours. The mixture is then cooled and concentrated under vacuum (30-80 torr) at an internal temperature at 25-40° C. (external temperature 30-45° C.) to collect about 980 g of solvent (batch volume about 300 mL). To the residue is added 1.6 L of toluene and the mixture is concentrated under vacuum (30-80 torr) at an internal temperature at 25-40° C. to collect 1250 g (1.4 L) of solvent (batch volume about 400 mL). This is repeated. To the residue is added 2.0 L of toluene, and the suspension stirred at an internal temperature at 22-26° C. for 30 minutes, then charged into a 12 L, 4-necked, round-bottomed flask, equipped with a mechanical stirrer, digital thermometer, reflux condenser, nitrogen inlet-outlet, and addition funnel. The suspension is diluted with 5.2 L of toluene. The mixture is heated to an internal temperature at 95-100° C. (external temperature 100-120° C.) over 30 minutes and stirred vigorously at this temperature for 2 hours. Afterwards, the mixture is cooled and the solids collected by filtration, and the filter cake washed with 0.4 L of toluene. The combined filtrates are concentrated under vacuum (30-80 torr) to collect 5.5 L of solvent (batch volume about 1.9 L). To the resulting mixture is added 7.0 L of heptane over a period of 2 hours while maintaining the internal temperature at 20-25° C. After stirring for 8 hours the solids are collected, washed with 0.6 L of heptane and dried under vacuum at 60-65° C. to obtain 148 g of crude 7-.tert.-butyl-6-(4-chlorophenyl)-2-thioxo-2,3-dihydro-1.H.-pyrido[2,3-.d.]-pyrimidin-4-one. A 12 L, 4-necked, round-bottomed flask, equipped with a mechanical stirrer, digital thermometer, reflux condenser, nitrogen inlet-outlet, and addition funnel is charged with the 148 g of crude 7-.tert.-butyl-6-(4-chlorophenyl)-2-thioxo-2,3-dihydro-1.H.-pyrido[2,3-.d.]-pyrimidin-4-one from the preceding step and 5.18 L of ethyl alcohol, 200 proof. The suspension is heated to an internal temperature at 76-80° C. (reflux condition, external temperature 85-100° C.) over 1 hour and stirred at this temperature for 2 hours to get a clear solution. The mixture is cooled to 70-75° C. over 20 minutes and linefiltered by pressure and saved. The solution is added into a 12 L, 4-necked, round-bottomed flask, equipped with a mechanical stirrer, digital thermometer, reflux condenser, nitrogen inlet-outlet, and addition funnel, and heated to 76-80° C. (reflux condition) over 30 minutes 3.11 L of water is added (ratio of ethanol:water: 1.0:0.6 v/v) over a period of 1.5 hours while maintaining the internal temperature at 76-83° C. (reflux condition, external temperature 90-115° C.). To this is added 0.09 g of pure 7-.tert.-butyl-6-(4-chlorophenyl)-2-thioxo-2,3-dihydro-1.H.-pyrido[2,3-.d.]-pyrimidin-4-one seeds in a mixture of 2 mL of water and 2 mL of ethanol at an internal temperature of 70-75° C. The reaction mixture is cooled, (crystals come out at about 65° C.) to 20-25° C. over 2 hours and stirred at this temperature for 12 hours. The solids are collected by filtration over a polypropylene filter paper in a Büchner funnel with suction; the filter cake is washed with 0.6 L of a mixture of ethyl alcohol and water (1:1 v/v) in two equal portions of 300 mL each. The solid is dried under vacuum (10-20 torr) at 60-65° C. with nitrogen bleeding until <0.5% LOD to obtain 96 g of 7-.tert.-butyl-6-(4-chlorophenyl)-2-thioxo-2,3-dihydro-1.H.-pyrido[2,3-.d.]-pyrimidin-4-one. Theoretical Yield: 224 g, Yield: 43% (over 3 steps). Purity: 98.4% (by HPLC Pd (0.02 ppm), toluene (0%), EtOH (0.01%), $H_2O$ (0.27%).

In the following examples compounds of formula I wherein $R^1$ and $R^2$ together are $-NR^{11}-C(O)-NR^{12}-C(O)-$ and $R^3$ is hydrogen are prepared analogously to the above Examples and exhibit the following characterizing data:

| NO. | $R^4$ | $R^5$ | $R^{11}$ | $R^{12}$ | HPLC [retention time in Min] |
|---|---|---|---|---|---|
| 1.1 | phenyl | ethyl | H | H | 7.19** |
| 1.2 | phenyl | ethyl | methyl | H | 8.16** |
| 1.3 | CN | tert.-butyl | H | H | 7.01** |
| 1.4 | 4-methylphenyl | tert.-butyl | H | H | 6.35*** |
| 1.5 | phenyl | tert.-butyl | H | H | 5.9* |

*LCMS - Kingsorb 3 micron C18 column, 30 mm x 4.6 mm; gradient elution 10% MeCN in water (+0.1% TFA) to 100% MeCN over 10 min
**HPLC-System: Column: Merck LiChrosphere 60 RP (RP C-18), solvents: A: $H_2O$, 0.1% TFA, B: $CH_3CN$, 0.1% TFA, gradient: 5 to 100% B in 10 min
***Phenomenex C18 R HPLC analytical column, 30 mm x 4.6 mm, gradient: 90:10 to 0:100 (water + 0.1% TFA:MeCN) 10 min In the following examples compounds of formula I wherein $R^1$ and $R^2$ together are $-NH-C(S)-NH-C(O)-$ and $R^3$ is hydrogen are prepared analogously to the above Examples and exhibit the following characterizing data:

| NO. | $R^4$ | $R^5$ | HPLC[retention time in Min] or melting data[in °] | NMR (DMSO) or MS data |
|---|---|---|---|---|
| 2.1 | phenyl | ethyl | 7.65** | |
| 2.2 | phenyl | tert.-butyl | 6.6* | 1.17(9H, s), 7.31(2H, m), 7.43(3H, m), 7.72 (1H, s), 12.5(0.3H-partially exchanged, br s), 13.0(0.3H-partially exchanged, br s) |
| 2.3 | 4-methylphenyl | tert.-butyl | 7.15*** | 1.16(9H, s), 2.37(3H, s), 7.18(2H, d, J=8.0Hz), 7.24(2H, d, J=8.0Hz), 7.70(1H, s), 12.5(0.8H-partially exchanged, br s), 13.1(0.8H-partially exchanged, br s) |

-continued

| NO. | R⁴ | R⁵ | HPLC [retention time in Min] or melting data [in °] | NMR (DMSO) or MS data |
|---|---|---|---|---|
| 2.4 | 4-bromophenyl | tert.-butyl | 7.23*** | 1.16(9H, s), 7.29(2H, d, J=8.3Hz), 7.63(2H, d, J=8.3Hz), 7.74(1H, s), 12.6(0.8H-partially exchanged, br s), 13.1 (0.8H-partially exchanged br s) |
| 2.5 | phenyl | cyclopropyl | 5.89*** | 1.03(2H, m), 1.17(2H, m), 2.10(1H, m), 7.52 (5H, m), 7.94(1H, s), 12.5(0.8H-partially exchanged, br s), 12.9 (0.8H-partially exchanged, br s) |
| 2.6 | 4-chlorophenyl | isopropyl | 6.8* | 1.16(6H, d, J=6.7Hz), 3.14(1H, m), 7.42(2H, d, J=8.4Hz), 7.56(2H, d, J=8.4Hz), 7.96(1H, s), 12.6(0.4H-partially exchanged, br s), 13.1 (0.4H-partially exchanged, br s) |
| 2.7 | 4-trifluoromethylphenyl | tert.-butyl | 7.24*** | [M+H]+=346/348 |
| 2.8 | 4-methoxyphenyl | tert.-butyl | 6.5*** | 1.17(9H, s), 3.81(3H, s), 6.99(2H, d, J=8.7Hz), 7.22(2H, d, J=8.7Hz), 7.71(1H, s), 12.6(0.2H-partially exchanged, br s), 13.1(0.2H-partially exchanged, br s) |
| 2.9 | 4-fluorophenyl | tert.-butyl | | 1.19(9H, s), 7.29(2H, m), 7.40(2H, m), 7.76 (1H, s); [M−H]⁻=328 |
| 2.10 | 2-chlorophenyl | tert.-butyl | 6.90*** | |
| 2.11 | 4-hydroxyphenyl | tert.-butyl | 5.25* | |
| 2.12 | phenyl | methyl | 274-275° C. | |
| 2.13 | 3-chlorophenyl | tert.-butyl | 7.07*** | [M+H]+=380 |
| 2.14 | 4-tert.-butylphenyl | tert.-butyl | 8.36*** | |
| 2.15 | 3-methoxyphenyl | tert.-butyl | 6.5* | |
| 2.16 | 4-fluorophenyl | isopropyl | | 1.17(6H, d), 3.16(1H, m), 7.33(2H, m), 7.45 (2H, m), 7.96(1H, s); [M−H]⁻=314 |

*LCMS - Kingsorb 3 micron C18 column, 30 mm × 4.6 mm; gradient elution 10% MeCN in water(+0.1% TFA) to 100% MeCN over 10 min
**HPLC-System: Column: Merck LiChrosphere 60 RP(RP C-18), solvents: A: H₂O, 0.1% TFA, B: CH₃CN, 0.1% TFA, gradient: 5 to 100% B in 10 min
***Phenomenex C18 R HPLC analytical column, 30 mm × 4.6 mm, gradient 90:10 to 0:100(water + 0.1% TFA: MeCN) over 10 min In the following examples compounds of formula I are prepared as described above by a variety of transformations and exhibit the following characterizing data:

| No. | R¹ and R² together | R³ | R⁴ | R⁵ | MS data | Melting data [°] |
|---|---|---|---|---|---|---|
| 3.1 | —N=C(Cl)—N=C(Cl)— | H | phenyl | tert.-butyl | EI – MS: [M − H]⁺ = 330, 332 | 135-136 |
| 3.2 | —NH—C(O)—N=C(Cl)— | H | phenyl | tert.-butyl | EI – MS: [M − H]⁺ = 312 | 176-179 |
| 3.3 | —NH—C(O)—N=C(OCH₃)— | H | phenyl | tert.-butyl | ES – MS: [M − H]⁻ = 308 | 254-256 (hydrochloride) |
| 3.4 | —NH—C(SCH₃)=N—C(O)— | H | phenyl | tert.-butyl | ES – MS: [M − H]⁻ = 324 | >250 |
| 3.5 | —N=C(Cl)—NH—C(O)— | H | phenyl | tert.-butyl | ES – MS: [M − H]−⁻ = 312; ES + MS: [MH]+⁻ = 314 | |
| 3.6 | —N=C(NH₂)—NH—C(O)— | H | phenyl | tert.-butyl | ES – MS: [M − H]⁻ = 293 | amorphous |

The invention claimed is:

1. A compound of formula (I)

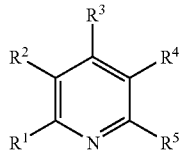

wherein
R$^1$ and R$^2$, together, are —NR$^{11}$—X—NR$^{12}$C(O)—, wherein X is C(O) or C(S), R$^{11}$ is hydrogen; C$_1$-C$_4$alkyl; C$_1$-C$_4$alkyl substituted by C(O)OC$_1$-C$_4$alkyl; or phenyl substituted by C$_1$-C$_4$alkyl; R$^{12}$ is hydrogen, NH$_2$ or phenyl substituted by C$_1$-C$_4$alkyl;
R$^3$ is hydrogen; OH; CN; C$_1$-C$_6$alkyl; phenyl; or C(O)OC$_1$-C$_4$alkyl;
R$^4$ is CN; phenyl; phenyl substituted by OH, halogen, C$_1$-C$_6$alkyl, C$_1$-C$_6$haloalkyl or C$_1$-C$_6$alkoxy; benzyl; benzoyl substituted by OH;
R$^5$ is C$_1$-C$_6$alkyl; C$_1$-C$_6$alkyl substituted by halobenzyl; C$_3$-C$_6$cycloalkyl; phenyl; or pyridinyl;
with the proviso that R$^1$ and R$^2$ together are not —NH—C(O)—NH—C(O)— when R$^3$ is phenyl, R$^4$ is —CN, and R$^5$ is —CH$_3$;
in free base or acid addition salt form.

2. A compound of formula (I)

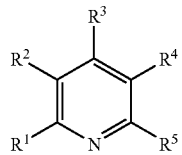

wherein
R$^1$ and R$^2$, together, are —NR$^{11}$—X—NR$^{12}$C(O)—, wherein X is C(O) or C(S), R$^{11}$ is hydrogen; C$_1$-C$_4$alkyl; C$_1$-C$_4$alkyl substituted by C(O)OC$_1$-C$_4$alkyl; or phenyl substituted by C$_1$-C$_4$alkyl; R$^{12}$ is hydrogen, NH$_2$ or phenyl substituted by C$_1$-C$_4$alkyl;
R$^3$ is hydrogen; OH; CN; C$_1$-C$_6$alkyl; phenyl; or C(O)OC$_1$-C$_4$alkyl;
R$^4$ is CN; phenyl; phenyl substituted by OH, halogen, C$_1$-C$_6$alkyl, C$_1$-C$_6$haloalkyl or C$_1$-C$_6$alkoxy; benzyl; benzoyl substituted by OH;
R$^5$ is C$_1$-C$_6$alkyl; C$_1$-C$_6$alkyl substituted by halobenzyl; C$_3$-C$_6$cycloalkyl; phenyl; or pyridinyl;
with the proviso that R$^1$ and R$^2$ together are not —NH—C(O)—NH—C(O)— when R$^3$ is phenyl, R$^4$ is —CN, and R$^5$ is —CH$_3$; and
with the proviso that R$^5$ does not represent C$_1$-C$_6$alkyl if R$^3$ is hydrogen, R$^4$ is phenyl and R$^1$ and R$^2$, together, form a radical —NR$^{11}$—X—NR$^{12}$C(O)—, wherein X is CO or CS and R$^{11}$ and R$^{12}$ are both hydrogen,
in free base or acid addition salt form.

3. A compound which is 7-tert-butyl-6-(4-chlorophenyl)-2-thioxo-2,3-dihydro-1H-pyrido[2,3-d]-pyrimidin-4-one in free base or acid addition salt form.

4. A process for the preparation of a compound of formula (I) as defined in claim 1, or a salt thereof, comprising the step of reacting a compound of formula (II)

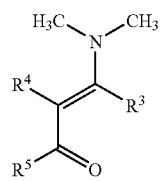

wherein R$^3$, R$^4$ and R$^5$ have the above meanings;
with a compound of formula (III)

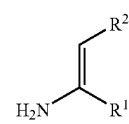

wherein R$^1$ and R$^2$ have the above meanings;
and recovering the obtained compound, in free base or in acid addition salt form.

5. A pharmaceutical composition comprising a compound of claim 1, in free base or pharmaceutically acceptable acid addition salt form, and a pharmaceutical carrier or diluent.

6. The process of making 7-tert-butyl-6-(4-chlorophenyl)-2-thioxo-2,3-dihydro-1H-pyrido[2,3-d]-pyrimidin-4-one or a salt thereof, comprising the steps of:
  i) preparing the compound 1-(4-chlorophenyl)-3,3-dimethyl-2-butanone by Pd-catalyzed arylation of pinacolone with 4-bromochlorobenzene in toluene in the presence of sodium t-butoxide; followed by treatment of the resulting intermediate with an aqueous solution of L-cysteine and sodium thiosulfate and azeotropic removal of water to produce the intermediate 2-(4-chlorophenyl)-1-(dimethylamino)-4,4-dimethyl-1-penten-3-one; which is then treated
  ii) with N,N-dimethylformamide dimethyl acetal and then
  iii) reacting the intermediate 2-(4-chlorophenyl)-1-(dimethylamino)-4,4-dimethyl-1-penten-3-one with 4-amino-6-hydroxy-2-mercaptopyrimidine monohydrate in toluene and acetic acid at 70° C. for 15 hours, then at 100° C. for 2 hours;
and purifying and recovering the obtained compound, in free base or in acid addition salt form.

* * * * *